United States Patent [19]

Wilschowitz

[11] Patent Number: 4,888,440

[45] Date of Patent: Dec. 19, 1989

[54] PROCESS FOR THE PREPARATION OF ASPARTIC ACID 4-(PHENYLMETHYL) ESTER

[75] Inventor: Ludwig Wilschowitz, Neuseass, Fed. Rep. of Germany

[73] Assignee: Diamalt AG, Munich, Fed. Rep. of Germany

[21] Appl. No.: 279,593

[22] PCT Filed: Mar. 17, 1988

[86] PCT No.: PCT/DE88/00183

§ 371 Date: Nov. 25, 1988

§ 102(e) Date: Nov. 25, 1988

[87] PCT Pub. No.: WO88/07520

PCT Pub. Date: Oct. 6, 1988

[30] Foreign Application Priority Data

Mar. 27, 1987 [DE] Fed. Rep. of Germany ....... 3710192

[51] Int. Cl.$^4$ ............................................. C07C 67/08
[52] U.S. Cl. ...................................... 560/171; 560/9; 560/22; 560/37; 560/170
[58] Field of Search .......................................... 560/171

[56] References Cited

U.S. PATENT DOCUMENTS

| | | | |
|---|---|---|---|
| 4,026,915 | 5/1977 | Billman et al. | 560/170 |
| 4,394,308 | 7/1983 | Sampathkumar et al. | 560/41 |
| 4,622,413 | 11/1986 | Krogh | 560/171 X |
| 4,709,086 | 11/1987 | Schlingmann et al. | 560/171 |
| 4,761,495 | 8/1988 | Wirth et al. | 560/41 |

FOREIGN PATENT DOCUMENTS 969132 9/1964 United Kingdom.

*Primary Examiner*—Werren B. Lone
*Assistant Examiner*—Vera C. Clarke
*Attorney, Agent, or Firm*—Millen, White & Zelano

[57] ABSTRACT

A process is described for the preparation of aspartic acid 4-(phenylmethyl) ester from aspartic acid and benzyl alcohol, characterized by utilizing a reaction mixture which contains, per mole of aspartic acid, 10–40 moles of benzyl alcohol and 1–5 moles of acetyl chloride, by conducting the reaction at a temperature of −10° C. to 50° C., and by separating the product of the process, after reaction has taken place, by neutralization with organic bases.

6 Claims, No Drawings

PROCESS FOR THE PREPARATION OF ASPARTIC ACID 4-(PHENYLMETHYL) ESTER

The invention relates to a process for the preparation of aspartic acid 4-(phenylmethyl) ester from aspartic acid and benzyl alcohol.

Such processes have been known previously (Houben-Weyl: "Methoden der organischen Chemie" [Methods of Organic Chemistry], Georg Thieme Publishers, D-Stuttgart, vol. XV/1, "Syntheses of Peptides, Part 1", 1974, pp. 645 et seq.). The most advantageous procedure for the partial esterification of aspartic acid with benzyl alcohol is deemed to be the condensation of the components, catalyzed by sulfuric acid. According to this process, it is assertedly possible to prepare the desired product of the process in a yield of 40–45% of theory (Can. J. Chem., 40: 571, 1962); however, it was found under practical conditions that the yields of the product of the process obtained according to this method are substantially lower. Furthermore, this conventional process has the drawback that the process per se and also the purification of the primarily obtained crude products, as well as the recovery of unreacted starting materials are rather expensive.

The present invention is based on the object of developing a process which is less expensive than the prior-art processes and which makes it possible to prepare the aspartic acid 4-(phenylmethyl) ester in a higher yield.

This object has been attained by making a process available which is characterized by using a reaction mixture containing, per mole of aspartic acid, 10–40 moles of benzyl alcohol and 1–5 moles of acetyl chloride; by performing the reaction at a temperature of −10° C. to 50° C.; and by separating the product of the process, after reaction has taken place, by neutralization with organic bases.

The process of this invention is suitable for the controlled esterification of the β-positioned carboxy groups of L-aspartic acid, of D-aspartic acid, and of D,L-aspartic acid.

In order to conduct the process of this invention, a reaction mixture is employed containing, per mole of aspartic acid, 10–40 (preferably 15–30 and especially 20–30) moles of benzyl alcohol and 1–5 (preferably 1–4 and especially 1.5–3.0) moles of acetyl chloride.

In accordance with the invention, the reaction is performed at −10° C. to +50° C. It proved to be expedient to conduct the reaction at a temperature of −10° C. to +20° C. (preferably −10° C. to +15° C. and especially at −5° C. to +10° C.), as long as the reaction still proceeds exothermally. In order to avoid overheating of the reaction mixture during this phase, the aspartic acid is suitably introduced in incremental portions under agitation into the provided benzyl alcohol - acetyl chloride mixture. The time required for this purpose is normally 1–4 hours. After termination of the exothermal reaction phase, the further reaction is suitably performed at a temperature of 10° C. to 50° C., preferably at 15°–30° C., and especially at room temperature. The required reaction period is, of course, dependent on the choice of the reaction temperature; this period can be readily determined by means of the customary analytical methods (e.g. by thin-layer chromatography). When performing the reaction after the exothermal phase at room temperature, the reaction time is normally 2–4 days.

After reaction has taken place, the reaction product will be precipitated by neutralization of the reaction mixture with organic bases (such as triethylamine, N-methylmorpholine and, in particular, pyridine). For this purpose, 1 mole of organic base is needed per mole of acetyl chloride utilized. The use of an excess of organic base is uncritical so that it is advantageous to employ 1 to 1.25 moles of organic base per mole of acetyl chloride utilized. Neutralization is usually performed at a temperature of 10°–40° C.—preferably at room temperature. For obtaining a complete precipitation of the product of the process (as the crude product), the neutralized mixture is suitably allowed to stand an additional 6–20 hours, if desired under cooling to 0° C. to 15° C.

After the crude product has been filtered, the excess benzyl alcohol and aspartic acid can be readily recovered from the filtrate in the following way: The filtrate is extracted with 3–7-molar aqueous sodium hydroxide solution. The organic phase is washed once again, dried, and the benzyl alcohol is obtained. The aqueous phase is acidified by means of acids to the isoelectric point of aspartic acid, the thus-precipitated aspartic acid is filtered off and dried. In this way, 9–10% of the aspartic acid utilized as the starting compound is recovered.

The crude aspartic acid 4-(phenylmethyl) ester product produced according to the method of this invention can be purified, for example, by recrystallization from water—to which 0.05–0.5% of pyridine has been added. In such a procedure, it is advantageous to concentrate the evolving filtrate under vacuum to dryness, to dissolve the resultant residue in 3–7molar aqueous sodium hydroxide solution, to acidify to the isoelectric point of aspartic acid, and in this way about 15–20% of the aspartic acid used as the starting material is recovered.

Accordingly, it is possible with the aid of the process according to this invention to produce the 4-(phenylmethyl) ester of aspartic acid in a yield of about 70% of theory, taking the recovered amounts of aspartic acid into account. This high yield of aspartic acid partially esterified in the 4-position is especially astonishing in view of the extraordinary excess of benzyl alcohol utilized for performing the process of this invention. Moreover, it is worth mentioning that the process of this invention offers quite considerable advantages under the antipollution aspect as compared with the prior-art methods.

The aspartic acid 4-(phenylmethyl) ester prepared by means of the process of this invention is, as is known, a valuable intermediate product which can serve, for example, for the synthesis of N-blocked aspartic acid 4-(phenylmethyl) esters, such as N-(phenylmethoxycarbonyl)aspartic acid 4-(phenylmethyl) ester, N[(4-methoxyphenyl)methoxycarbonyl]aspartic acid 4-(phenylmethyl) ester, N-[(2-nitrophenyl)sulfenyl]aspartic acid 4-(phenylmethyl) ester, N-(tert-butoxycarbonyl)aspartic acid 4-(phenylmethyl) ester, or N-(tert-amyloxycarbonyl)aspartic acid 4-(phenylmethyl) ester; these compounds, in turn, are valuable intermediates for the production of peptides.

Thus, it is possible, for example, to convert the aspartic acid 4-(phenylmethyl) ester, under the conditions of the practical example that seem very expedient, into the N-(phenylmethoxy)carbonylaspartic acid 4-(phenylmethyl) ester which, as is known, is inter alia a valuable intermediate product for the synthesis of N-α-apartylphenylalanine methyl ester (aspartame).

The examples set forth below serve as a more detailed explanation of the invention.

Practical Example Concerning the Process of This Invention

A solution of 132.6 g (1.69 mol) of acetyl chloride in 2,500 ml (24.04 mol) of benzyl alcohol is cooled to 0° C. and combined under agitation with incremental portions of 133.1 g (1.00 mol) of L-aspartic acid (dried over calcium chloride). The mixture is stirred for 3 days at room temperature.

The resultant solution is combined with 133.3 g (1.68 mol) of pyridine in incremental portions, and then agitated for 12 hours at room temperature. Then the separated product is suctioned off.

The thus-obtained filtrate is extracted with 5N aqueous sodium hydroxide solution, the aqueous phase is set at pH 2.77 with dilute aqueous hydrochloric acid. The mixture is stirred for 2 hours at room temperature. The thus-separated aspartic acid is washed with water and 2-propanol, dried over calcium chloride, and the yield is 12.73 g of aspartic acid=9.5% of theory.

The thus-obtained crude product is washed with methyl tert-butyl ether and dried under vacuum. Then it is dissolved in hot water to which several drops of pyridine have been added, the solution is filtered in the hot state, and, after cooling, stored for 12 hours at 5° C.

The separated crystals are suctioned off, washed with water, and dried under vacuum over calcium chloride.

Yield: 116.0 g of L-aspartic acid 4-(phenylmethyl) ester, mp 206°–207° C. (decomposition).

The crystallization mother liquor is combined with the washing liquid and, at a bath temperature of 30°–40° C., concentrated to dryness under vacuum. The residue is dissolved in 5N aqueous sodium hydroxide solution. The resultant solution is adjusted to pH 2.77 with dilute aqueous hydrochloric acid and stirred for one hour at room temperature. The thus-precipitated aspartic acid is filtered off, washed with water and 2-propanol, and dried under vacuum over calcium chloride, thus obtaining 21.7 g of L-aspartic acid.

Practical Example Concerning the Further Processing of the Product

Under agitation, 1.05 g (10 millimoles) of sodium carbonate is introduced at 0° C. into a suspension of 4.46 g (20 mmol) of L-aspartic acid 4-(phenylmethyl) ester in 160 ml of water. Then, within one hour, under agitation at 0° C., 4.93 g (26 mmol) of benzyl chloroformate (90% strength) and a solution of 1.38 g (13 mmol) of sodium carbonate in 25 ml of water are added simultaneously. The mixture is stirred for 3 hours at room temperature, methyl tert-butyl ether is extracted, and the aqueous phase is acidified with hydrochloric acid to pH 2–2.5 at 0° C. An oil separates which crystallizes after a short period of time. After standing for 12 hours at 5° C., the thus-separated crystals are suctioned off, washed with water, and dried under vacuum over calcium cloride.

Yield: 6.04 g of N-(phenylmethoxy)carbonylaspartic acid 4-(phenylmethyl) ester=84% of theory.

I claim:

1. A process for preparing aspartic acid 4-(phenylmethyl) ester from aspartic acid and benzyl alcohol, comprising
    reacting 10–40 moles of benzyl alcohol and 1–5 moles of acetyl chloride per mole of aspartic acid;
    conducting the reaction at a temperature of 31 10° C. to 50° C.; and
    separating the thus-formed aspartic acid 4-(phenylmethyl) ester by neutralization with an organic base.

2. A process according to claim 1, wherein the reaction is conducted at −10° C. to +20° C. while the reaction is in an exothermal phase.

3. A process according to claim 1, wherein the remainder of the reaction, after the exothermal phase is complete, is conducted at 10° C. to 50° C.

4. A process according to claim 1, wherein the organic base is triethylamine, N-methylmorpholine or pyridine.

5. A process according to claim 4, wherein the organic base is pyridine.

6. A process according to claim 1, further comprising recrystallizing the thus-formed aspartic acid 4-(phenylmethyl) ester from a 0.05 to 0.5% solution of pyridine in water.

* * * * *

UNITED STATES PATENT AND TRADEMARK OFFICE
CERTIFICATE OF CORRECTION

PATENT NO. : 4,888,440

DATED : December 19, 1989

INVENTOR(S) : LUDWIG WILSCHOWITZ

It is certified that error appears in the above-identified patent and that said Letters Patent is hereby corrected as shown below:

Column 4, claim 1, line 26:

reads "conducting the reaction at a temperature of 31 10° C."

should read -- conducting the reaction at a temperature of -10° C. --

Signed and Sealed this

Eleventh Day of December, 1990

*Attest:*

HARRY F. MANBECK, JR.

*Attesting Officer*     *Commissioner of Patents and Trademarks*